United States Patent [19]

Tomatis

[11] Patent Number: Plant 5,611

[45] Date of Patent: Dec. 24, 1985

[54] RANUNCULUS PLANT—FEVER

[76] Inventor: Simon Tomatis, 451 Chemin St Elisabeth, 06140 Vence, France

[21] Appl. No.: 565,883

[22] Filed: Dec. 27, 1983

[30] Foreign Application Priority Data

Dec. 27, 1982 [FR] France ..... 82 21968

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Young & Thompson

[57] ABSTRACT

A ranunculus plant having bright red blossoms borne on long, straight stems.

1 Drawing Figure

The present invention relates to a new variety of *Ranunculus asiaticus* called Fever which the inventor has produced in the course of his studies and research aimed at finding new products capable of increasing the profits of horticulturists, either by readier sales of the flowers, or by greater productivity of the plants.

The new variety which is the object of the present invention is different from all other ranunculus known heretofore, and constitutes, with respect to the latter, an improvement, either by the shape and the color of the flower, or by the very high productivity of the plants.

The new variety which is the object of the present invention has been obtained by artificially fertilizing flowers of the known commercial variety called "BARBAROUX", with red flowers, with pollen of the variety "PINK PERFECTION", with pink flowers. From the mother variety "BARBAROUX", the new variety has taken much of its color, which is however brighter than that of the mother variety, by reason of the larger dimensions of the corollas. From the father variety, "PINK PERFECTION", the new variety has taken the vegetative carriage, resulting in plants that are very tall and slender and very productive in cut flowers.

As a result, the new variety constitutes a new product adapted to be commercially cultured for the production of cut flowers for market.

The new variety which is the object of the present invention may be easily reproduced in any number of offspring which are altogether identical with the original plant, by means of division of the tuberous roots which each plant naturally produces, and by then cultivating them either in the open air or under glass.

The plant described in the description which follows has been cultivated under glass, planted in the months of August–September, and described as of the month of December. One must always refer to these conditions of season and culture, each time it is desired to compare the plant with the present description. Ultimate differences which, by reason of different climate or culture conditions, may arise between certain characteristics of the plant and the corresponding characteristics of the description, should be considered as normal and do not modify the essence of the present invention, the less so because it is possible to identify the plant by means of the totality of the characteristics given in the description.

The identification of the colors of the description was made in accordance with the tables of the "Royal Horticultural Society Colour Chart" of London (indicated in the text by the initials R.H.S., followed by the number of the table).

PLANT

Origin: "BARBAROUX"×"PINK PERFECTION".

Vegetative carriage: Robust plant, vegetation erect, slender, thin.

Length: From the base to the floral button: 70–80 cm.

Roots: Tuberous to the collar, surrounded by numerous roots, thin, 10–15 cm long and of a mean diameter of 0.5–2 mm.

Floral stems: Averaging 3 to 6, emerging from the base of the plant, straight, upright, rigid.

*Carriage.*—Upright.

*Dimensions.*—Average length 65–80 cm. Average diameter 5–8 mm.

*Nodes.*—Not very numerous, very elongated, average spacing 25–40 cm.

*Surface.*—Glossy, a little tomentose.

*Color.*—Green (R.H.S. 144 A-B).

Leaves: Usually numerous, emerging from the base of the plant or inserted at the nodes of the floral stems having a long peduncle up to 20–30 cm, thin, rigid.

*Border.*—Generally divided in three parts of which one is longer, and in turn divided in lobes in the form of straight fan shape, with toothed borders generally toward the point.

*Texture.*—Herbaceous, thick.

*Surface.*—Upper surface glossy, glabrous, with radial veins, plunging into the limb. Lower surface opaque, a little tomentose, with radial veins raised on the limb.

*Color.*—Upper surface dark green (R.H.S. 137 ABC) Lower surface lighter green (R.H.S. 138 A).

*Dimensions.*—Penduncle, length 15–25 cm, diameter 2–3 mm. Limb, length 6–10 cm, width 6–7 cm.

FLOWER

Carriage: Upright, terminal on the floral stem.

Flower button: Of medium dimensions, flattened globular, with sharp point.

*Dimensions.*—Length 12–15 mm, diameter 12–18 mm.

*Color.*—At the opening of the sepals, red (R.H.S. 45A).

Corolla: Round, regular, in the form of a flat section with slightly festooned edges.

*Overall color.*—Light red (R.H.S. 44A) tinged with orange (R.H.S. 34A) on the edges of the outer petals.

*Mean dimensions.*—Diameter 35–50 mm, length 15–25 mm.

Sepals: Average 5–7, triangular lanceolate, downwardly curved on the peduncle, upwardly concave.

*Mean dimensions.*—Length 12–15 mm, width 4–6 mm.

*Edges.*—Unitary, tomentose.

*Surface.*—Upper surface, a little tomentose. Lower surface, a little tomentose.

*Color.*—Gray green, upper surface (R.H.S. 143 B) lower surface (R.H.S. 138 A).

*Texture.*—Thin, translucent.

Petals: Very numerous, averaging 80–100, imbricated, disposed on the receptacle in very tight verticils.

*Shape.*—Very rounded fan shape. Robust claw moderately differentiated.

*Dimensions.*—Quite variable according to the position in the corolla, decreasing from the exterior toward the center. Length 15–20, width 20–25 (external petal).

*Color.*—Upper surface, light red (R.H.S. 34 A) with tinges of orange (R.H.S. 38 A) on the outer edges of the petals. Lower surface, bright red (R.H.S. 34 AB) tinted orange (R.H.S. 38 AB).

*Texture.*—Thin, resistant.

*Surface.*—Upper surface silky, lower surface silky.

REPRODUCTIVE ORGANS

Stamens: Almost completely transformed as petals. In certain flowers at the end of the flowering it is possible to find fertile stamens.

Ovary: Small, raised.

Pistils: Moderately numerous, short, locked together, at the center of the corolla, almost completely covered by the central petals.

Odor: None.

Resistance to disease: Very good.

Resistance to transport: Very good.

Durability of the cut flower: Very good.

Flowering: Very abundant, early.

I claim:

1. The new and distinct variety of ranunculus, as described and illustrated.

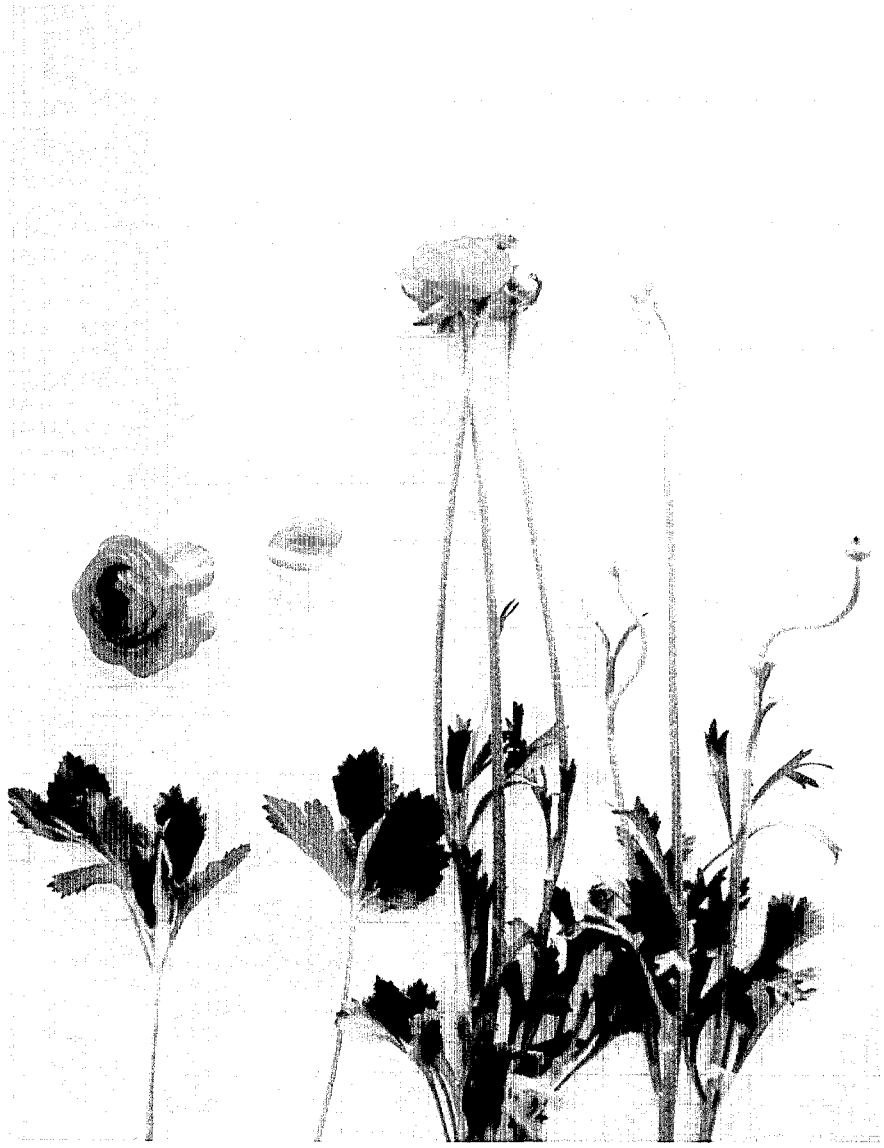

* * * * *